US012765864B2

United States Patent
(12) United States Patent
Matsuda

(10) Patent No.: US 12,765,864 B2
(45) Date of Patent: Oct. 20, 2026

(54) ULTRASOUND DIAGNOSTIC APPARATUS AND DATA PROCESSING METHOD

(71) Applicant: FUJIFILM Healthcare Corporation, Kashiwa (JP)

(72) Inventor: Fumie Matsuda, Chiba (JP)

(73) Assignee: FUJIFILM Corporation, Tokyo (JP)

( * ) Notice: Subject to any disclaimer, the term of this patent is extended or adjusted under 35 U.S.C. 154(b) by 33 days.

(21) Appl. No.: 18/502,379

(22) Filed: Nov. 6, 2023

(65) Prior Publication Data

US 2024/0156437 A1 May 16, 2024

(30) Foreign Application Priority Data

Nov. 16, 2022 (JP) ................................ 2022-183240

(51) Int. Cl.
*A61B 8/00* (2006.01)

(52) U.S. Cl.
CPC ................ *A61B 8/463* (2013.01); *A61B 8/54* (2013.01)

(58) Field of Classification Search
CPC .. A61B 8/463; A61B 8/54; A61B 8/44; A61B 8/4488; A61B 8/5215; A61B 8/5261; G16H 30/20; G16H 40/67
See application file for complete search history.

(56) References Cited

U.S. PATENT DOCUMENTS 5,840,018 A * 11/1998 Michaeli .............. A61B 8/0816 600/300
6,063,030 A * 5/2000 Vara ....................... A61B 8/465 600/440
6,261,234 B1 * 7/2001 Lin ........................ A61B 8/445 600/463
6,468,212 B1 * 10/2002 Scott ...................... A61B 8/463 600/440
9,072,471 B2 * 7/2015 Kato ...................... A61B 8/462
9,402,601 B1 * 8/2016 Berger ................... G16H 40/67
(Continued)

FOREIGN PATENT DOCUMENTS

CN 105101881 A 11/2015
CN 105142493 A 12/2015
(Continued)

OTHER PUBLICATIONS

Jun. 30, 2026 Japanese official action (and English-language translation thereof) in connection with Japanese Patent Application No. 2022-183240.

(Continued)

*Primary Examiner* — Sanjay Cattungal

(57) ABSTRACT

In an ultrasound diagnostic apparatus, a data group acquired from a server is prevented from being stored in a local storage unit for a long time. An acquisition section acquires a data group from a server and stores the data group in a storage unit (local storage unit). A display controller juxtaposes and displays, during execution of a multi-image display mode, a real-time ultrasound image generated through transmission and reception of an ultrasound wave and a reference image generated based on data selected from the data group. A deletion section automatically deletes data satisfying a deletion condition within the data group from the storage unit at an end of the multi-image display mode.

13 Claims, 6 Drawing Sheets

(56) References Cited

U.S. PATENT DOCUMENTS

| | | | | | |
|---|---|---|---|---|---|
| 2002/0103437 | A1* | 8/2002 | Jibiki | G01S 15/8988 | 600/454 |
| 2003/0179915 | A1* | 9/2003 | Goto | G06T 7/12 | 382/128 |
| 2003/0195418 | A1* | 10/2003 | Barnes | A61B 8/462 | 600/437 |
| 2004/0120561 | A1* | 6/2004 | Goto | G06T 7/0012 | 382/128 |
| 2004/0267116 | A1* | 12/2004 | Flood | A61B 8/0866 | 600/443 |
| 2005/0085730 | A1* | 4/2005 | Flesch | A61B 8/12 | 600/459 |
| 2006/0020204 | A1* | 1/2006 | Serra | G01S 7/5208 | 600/437 |
| 2007/0253531 | A1* | 11/2007 | Okuzawa | G06T 5/40 | 378/62 |
| 2008/0269607 | A1* | 10/2008 | Ishida | A61N 7/02 | 600/439 |
| 2009/0209859 | A1* | 8/2009 | Tsujita | A61B 8/08 | 600/445 |
| 2009/0306514 | A1* | 12/2009 | Imamura | G01S 7/52073 | 600/458 |
| 2010/0002919 | A1* | 1/2010 | Kargar | G06F 16/51 | 382/128 |
| 2010/0160787 | A1* | 6/2010 | Gorzitze | A61M 5/427 | 600/461 |
| 2010/0217128 | A1* | 8/2010 | Betts | A61B 8/4254 | 345/184 |
| 2011/0306869 | A1* | 12/2011 | Hwang | A61B 8/4416 | 600/443 |
| 2012/0133601 | A1* | 5/2012 | Marshall | G06F 3/041 | 345/173 |
| 2012/0183188 | A1* | 7/2012 | Moriya | G16H 30/20 | 382/128 |
| 2013/0120524 | A1* | 5/2013 | Zheng | H04N 5/265 | 348/36 |
| 2013/0226001 | A1* | 8/2013 | Steen | G01S 7/52096 | 600/447 |
| 2013/0239052 | A1* | 9/2013 | Moody | G06F 3/017 | 715/810 |
| 2013/0324850 | A1* | 12/2013 | Petruzzelli | A61B 8/465 | 600/407 |
| 2014/0051984 | A1* | 2/2014 | Berger | A61B 18/02 | 600/424 |
| 2014/0121524 | A1* | 5/2014 | Chiang | A61B 8/0841 | 600/459 |
| 2014/0221837 | A1* | 8/2014 | Park | A61B 8/085 | 604/117 |
| 2014/0243669 | A1* | 8/2014 | Halmann | G01S 7/5208 | 600/443 |
| 2015/0265252 | A1* | 9/2015 | Chu | A61B 8/461 | 600/431 |
| 2016/0119743 | A1* | 4/2016 | Oh | H04L 41/0803 | 455/41.2 |
| 2016/0247485 | A1* | 8/2016 | Bryce | G06T 11/60 | |
| 2016/0267221 | A1* | 9/2016 | Larcom | G16H 70/00 | |
| 2017/0150948 | A1* | 6/2017 | Kanayama | A61B 8/488 | |
| 2018/0234497 | A1* | 8/2018 | Ueda | H04L 67/12 | |
| 2019/0005662 | A1* | 1/2019 | Hirakawa | G06T 7/73 | |
| 2020/0281542 | A1* | 9/2020 | Irish | G16H 30/20 | |
| 2021/0153808 | A1* | 5/2021 | Tada | A61B 6/032 | |
| 2021/0275121 | A1* | 9/2021 | McLaughlin | A61B 6/032 | |
| 2021/0350906 | A1* | 11/2021 | Janicki | G06F 3/0483 | |
| 2023/0132148 | A1* | 4/2023 | Sowards | A61B 8/0841 | 600/437 |
| 2023/0138970 | A1* | 5/2023 | Sowards | A61B 8/488 | 600/437 |
| 2023/0255602 | A1* | 8/2023 | Aase | A61B 8/485 | 705/2 |
| 2024/0156437 | A1* | 5/2024 | Matsuda | A61B 8/463 | |

FOREIGN PATENT DOCUMENTS

| | | | |
|---|---|---|---|
| CN | 106456135 | A | 2/2017 |
| JP | 2004-057356 | A | 2/2004 |
| JP | 2008-183245 | A | 8/2008 |
| JP | 2011-005039 | A | 1/2011 |
| JP | 2011-154705 | A | 8/2011 |
| JP | 2011-258090 | A | 12/2011 |
| JP | 2012-034811 | A | 2/2012 |

OTHER PUBLICATIONS

Aug. 12, 2026 Chinese official action (and English-language translation thereof) in connection with Chinese Patent Application No. 2023115197632.

* cited by examiner 62, 64, 66, 68, 70, 72, 74, 76

| DATA ID | SUBJECT ID | NAME | EXAMINATION DATE | MODALITY TYPE | DATA TYPE | ··· |
|---|---|---|---|---|---|---|
| ******* | ******* | ******* | ******* | CT | 3D | ··· |
| ******* | ******* | ******* | ******* | MR | 3D | ··· |
| ******* | ******* | ******* | ******* | US | 2D | ··· |
| ··· | ··· | ··· | ··· | | ··· | ··· |

50, 78, 80, 82, 84, 86, 88, 90

| SUBJECT ID | NAME | EXAMINATION DATE | MODALITY TYPE | DATA TYPE | ··· | OPERATION FLAG |
|---|---|---|---|---|---|---|
| ******* | ******* | ******* | CT | 3D | ··· | 0 |
| ******* | ******* | ******* | CT | 3D | ··· | 1 |
| ******* | ******* | ******* | MR | 3D | ··· | 0 |
| ******* | ******* | ******* | MR | 3D | ··· | 0 |

ULTRASOUND DIAGNOSTIC APPARATUS AND DATA PROCESSING METHOD

CROSS-REFERENCE TO RELATED APPLICATION

The present application claims priority from Japanese patent application 2022-183240 filed on Nov. 16, 2022, the content of which is hereby incorporated by reference into this application.

BACKGROUND OF THE INVENTION

1. Field of the Invention

The present disclosure relates to an ultrasound diagnostic apparatus and a data processing method, and more particularly, to processing of data acquired from a server.

2. Description of the Related Art

An ultrasound diagnostic apparatus is utilized in an ultrasound examination of a subject. The ultrasound diagnostic apparatus is provided with a mode for simultaneously displaying a plurality of images. Hereinafter, the mode will be referred to as a multi-image display mode, and a display pattern configured by this function will be referred to as a multi-image display.

The plurality of images displayed in the multi-image display mode are an ultrasound image and a reference image to be compared with the ultrasound image. Usually, those images represent the same tissue. The ultrasound image is a real-time ultrasound image displayed as a video image, and the reference image is, for example, an ultrasound image (usually a still image) acquired in the past or a non-ultrasound image (usually a still image) acquired in the past.

Examples of the non-ultrasound image include a CT image acquired by a CT apparatus, an MR image acquired by an MRI apparatus, and the like. In practice, the CT image serving as the reference image is generated based on cross-section data cut out from volume data obtained by the CT apparatus, and the MR image serving as the reference image is generated based on cross-section data cut out from volume data obtained by the MRI apparatus. The reference image may also be generated based on cross-section data cut out from volume data acquired by the same or another ultrasound diagnostic apparatus.

JP2012-34811A discloses a system including a medical apparatus and a server. After the completion of uploading an image from the medical apparatus to the server, the image is automatically deleted from the medical apparatus. JP2011-5039A discloses an ultrasound diagnostic apparatus. In the ultrasound diagnostic apparatus, data related to a user designation is automatically deleted at a point in time when the set date and time arrive. JP2012-34811A and JP2011-5039A do not disclose a technique for automatically deleting data with low storage necessity upon the end of a specific function in the ultrasound diagnostic apparatus.

SUMMARY OF THE INVENTION

In order to smoothly start a multi-image display in an ultrasound diagnostic apparatus, it is desirable to acquire a data group with potential for use from a server in advance or early and store that data group in a local storage unit. However, in a case where a storage state of the data group persists for a prolonged period, the effective utilization of the limited storage space of the local storage unit becomes compromised.

An object of the present disclosure is to prevent a data group acquired from a server from being stored in a local storage unit for a long time.

According to an aspect of the present disclosure, there is provided an ultrasound diagnostic apparatus comprising: an acquisition section configured to acquire a data group from a server and store the data group in a local storage unit; a controller configured to display, during execution of a multi-image display mode, a real-time ultrasound image generated through transmission and reception of an ultrasound wave and a reference image generated based on data selected from the data group stored in the local storage unit; and a deletion section configured to delete data satisfying a deletion condition within the data group stored in the local storage unit from the local storage unit at or after an end of the multi-image display mode.

According to another aspect of the present disclosure, there is provided a data processing method comprising: a step of acquiring a data group from a server and storing the data group in a local storage unit; a step of displaying, during execution of a multi-image display mode, a real-time ultrasound image generated through transmission and reception of an ultrasound wave and a reference image generated based on data selected from the data group stored in the local storage unit; and a step of deleting data satisfying a deletion condition within the data group stored in the local storage unit from the local storage unit at or after an end of the multi-image display mode.

According to the aspects of the present disclosure, an advantage of preventing the data group acquired from the server from being stored in the local storage unit for a long time can be obtained.

DESCRIPTION OF THE PREFERRED EMBODIMENTS

Figure 1:
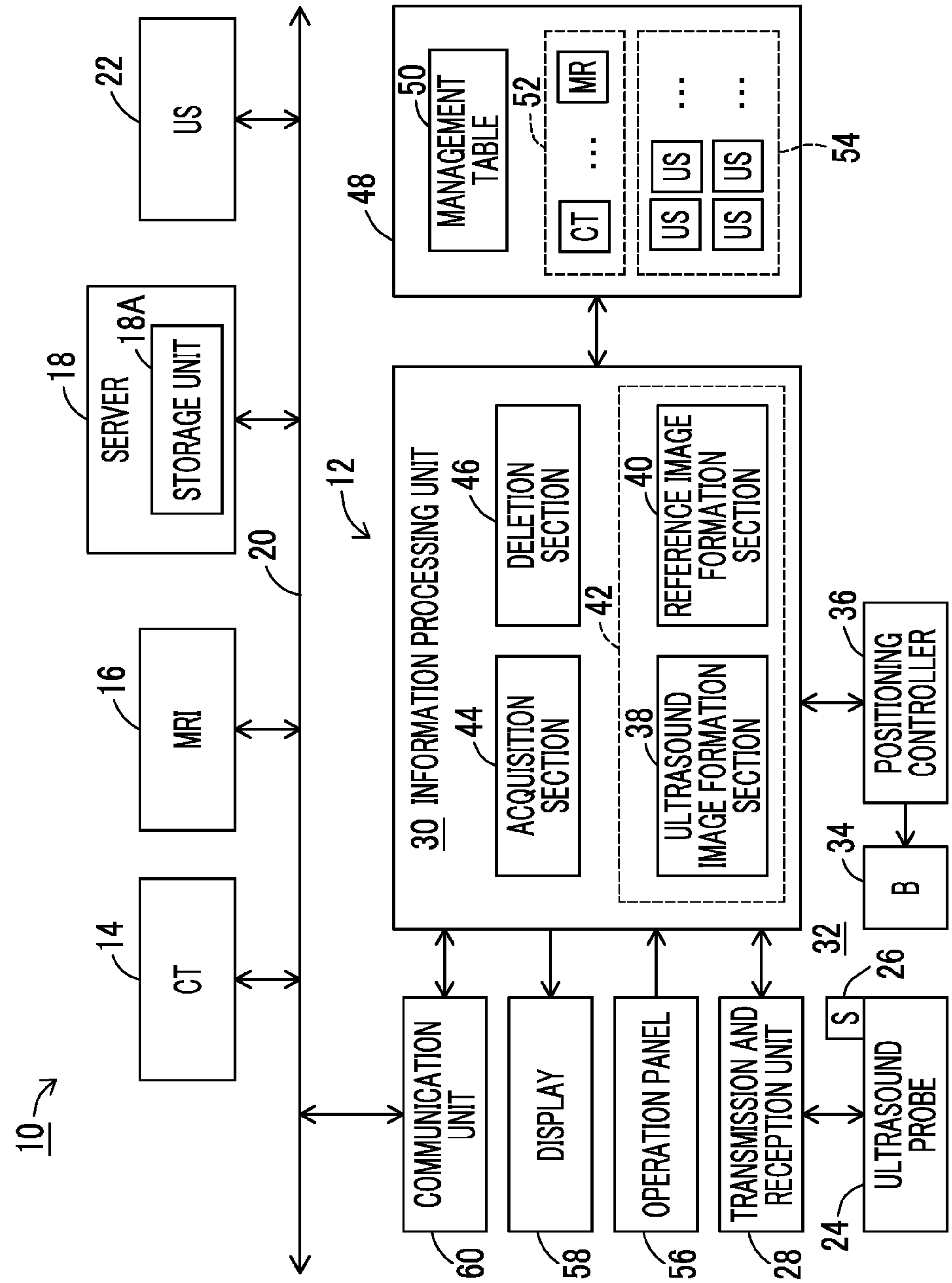
FIG. 1 is a block diagram showing a configuration example of an ultrasound diagnostic apparatus according to an embodiment.

Hereinafter, an embodiment will be described with reference to the drawings.

(1) Outline of Embodiment

An ultrasound diagnostic apparatus according to the embodiment includes an acquisition section, a controller, and a deletion section. The acquisition section acquires a data group from a server and stores the data group in a local storage unit. The controller displays, during execution of a multi-image display mode, a real-time ultrasound image generated through transmission and reception of an ultrasound wave and a reference image generated based on data selected from the data group stored in the local storage unit. The deletion section deletes data satisfying a deletion condition within the data group stored in the local storage unit from the local storage unit at or after an end of the multi-image display mode.

According to the above-described configuration, since the data satisfying the deletion condition is deleted at or after the end of the multi-image display mode, wasteful consumption of the limited storage space of the local storage unit can be prevented. Since the deletion of the data satisfying the deletion condition is automatically executed, there is no burden on the user in terms of deletion operations. The above-described controller functions as a display controller or a display processing unit.

It is also conceivable to uniformly delete the entire data group at the end of the multi-image display mode, but in that case, in a case where the multi-image display mode is executed again during the ultrasound examination, the same data need to be acquired again. In consideration of this, the storage state of data (that is, data satisfying a retention condition) other than the data satisfying the deletion condition is maintained at or after the end of the multi-image display mode. It is also conceivable to delete the data group all at once at the end of the ultrasound examination, but it is preferable to delete the data satisfying the deletion condition at the end of the multi-image display mode in order to expedite storage space release.

In the embodiment, the data group includes volume data obtained from within a body of a specific subject. The real-time ultrasound image represents a tissue on a beam scanning plane formed within the body of the specific subject. In the multi-image display mode, cross-section data corresponding to the beam scanning plane is extracted from volume data serving as the selected data, and the reference image is generated and displayed based on the cross-section data.

In a case where an ultrasound probe is moved, the beam scanning plane moves accordingly. The content of the reference image is updated in conjunction with the movement of the beam scanning plane. According to the multi-image display mode, it is possible to perform diagnosis or evaluation of the tissue while comparing the real-time ultrasound image with the reference image (a non-ultrasound image or an ultrasound image). The reference image is a CT image, an MR image, a PET image, or the like. In the embodiment, a positioning system is incorporated into the ultrasound diagnostic apparatus in order to obtain position information of the ultrasound probe.

In the embodiment, the deletion section deletes the data satisfying the deletion condition from the local storage unit at the end of the multi-image display mode, and deletes data remaining within the data group stored in the local storage unit at the end of the ultrasound examination including a step of executing the multi-image display mode. According to this configuration, since the data is deleted in a stepwise manner, it is possible to achieve both the storage space release and the smooth utilization of the data.

In the embodiment, the deletion section deletes the data satisfying the deletion condition from the local storage unit at or after the end of the multi-image display mode, only in a case where the data group is acquired from the server during the execution of the multi-image display mode. In a case where the data group is acquired from the server irrespective of the multi-image display, there is a probability of using the data group in other application programs. Therefore, the preservation of the data group is prioritized.

The ultrasound diagnostic apparatus according to the embodiment includes a management table in which, for each data constituting the data group, a flag indicating the presence or absence of a predetermined operation on the data during the execution of the multi-image display mode is registered. The deletion section specifies the data satisfying the deletion condition by referring to the management table. This configuration is for determining the necessity to retain data in accordance with the presence or absence of the predetermined operation.

In the embodiment, the deletion section has a first deletion function of deleting the data satisfying the deletion condition from the local storage unit at the end of the multi-image display mode, and a second deletion function of deleting the entire data group from the local storage unit at the end of the multi-image display mode. Either the first deletion function or the second deletion function is selected by the user. According to this configuration, it is possible to selectively execute the first deletion function or the second deletion function according to the necessity of data storage, the size of the available storage space of the local storage unit, and the like.

A data processing method according to the embodiment includes an acquisition step, a display step, and a deletion step. In the acquisition step, the data group is acquired from the server, and the data group is stored in the local storage unit. In the display step, during execution of the multi-image display mode, the real-time ultrasound image generated through transmission and reception of an ultrasound wave and the reference image generated based on data selected from the data group stored in the local storage unit are displayed. In the deletion step, the data satisfying the deletion condition within the data group stored in the local storage unit is deleted from the local storage unit at or after the end of the multi-image display mode.

(2) Details of Embodiment

FIG. 1 shows an ultrasound diagnostic system 10 according to the embodiment. The ultrasound diagnostic system 10 is installed in, for example, a medical institution such as a hospital. In the shown example, the ultrasound diagnostic system 10 includes an ultrasound diagnostic apparatus 12, a CT apparatus 14, an MRI apparatus 16, a server 18, and the like. These apparatuses are connected to each other via a network 20. Another ultrasound diagnostic apparatus 22 is also connected to the network 20.

The data acquired by the ultrasound diagnostic apparatuses 12 and 22 is uploaded to the server 18. Similarly, the data acquired by the CT apparatus 14 and the MRI apparatus 16 is uploaded to the server 18. In the embodiment, the volume data is sent from the CT apparatus 14 to the server 18, and the volume data is sent from the MRI apparatus 16 to the server 18. The volume data may be sent from the other ultrasound diagnostic apparatus 22 to the server. The volume data is three-dimensional data acquired from a three-dimensional space within the subject and is usually a collection of a plurality of pieces of slice data. The server 18 includes a storage unit 18A that stores a plurality of pieces of uploaded data. The storage unit 18A is composed of a semiconductor memory, a hard disk, or the like.

The ultrasound diagnostic apparatus 12 includes an ultrasound probe 24. The ultrasound probe 24 includes a transducer array that transmits and receives an ultrasound wave. The transducer array is composed of a plurality of transducers arranged one-dimensionally. An ultrasound beam is formed by the transducer array, and the ultrasound beam is electronically scanned. As the electronic scanning method, an electronic linear scanning method, an electronic sector scanning method, and the like are known. A two-dimensional transducer array is provided inside the ultrasound probe 24, as necessary.

The ultrasound probe 24 is provided with a magnetic sensor 26. The magnetic sensor 26 detects a magnetic field generated by a magnetic field generator 34. A signal from a positioning controller 36 is supplied to the magnetic field generator 34. A positioning system is composed of the magnetic sensor 26, the magnetic field generator 34, and the positioning controller 36. The positioning system generates position information indicating a position and an orientation of the ultrasound probe.

A transmission and reception unit 28 is composed of a transmission unit and a reception unit. Specifically, the transmission unit is composed of an electronic circuit serving as a transmission beamformer and supplies a plurality of transmission signals in parallel to the transducer array during the transmission. As a result, a transmission beam is formed. The reception unit is composed of an electronic circuit serving as a reception beamformer and applies phase addition to a plurality of reception signals output in parallel from the transducer array during the reception. As a result, reception beam data is generated.

A beam scanning plane is formed within the body of the subject through electronic scanning of the ultrasound beam. The beam scanning plane is a two-dimensional data acquisition region. A plurality of pieces of reception beam data arranged in an electronic scanning direction are generated during each electronic scanning of the ultrasound beam. Reception frame data is composed of the plurality of pieces of reception beam data. Each reception beam data is composed of a plurality of pieces of echo data arranged in a depth direction. By repeating the electronic scanning of the ultrasound beam, a plurality of pieces of reception frame data are generated, and these are sent to an information processing unit 30. One piece of reception frame data corresponds to one piece of two-dimensional data acquired from the beam scanning plane.

The beam scanning plane moves within a living body with the movement of the ultrasound probe 24. The above-described positioning system is provided in order to specify a position and an orientation of the beam scanning plane.

The information processing unit 30 is composed of one or a plurality of processors. For example, the information processing unit 30 is composed of a CPU that executes a program. In FIG. 1, a plurality of functions exhibited by the information processing unit 30 are represented by a plurality of blocks.

The information processing unit 30 functions as an ultrasound image formation section 38, a reference image formation section 40, an acquisition section 44, and a deletion section 46. A display controller 42 realizes the multi-image display in the multi-image display mode. The display controller 42 includes the ultrasound image formation section 38 and the reference image formation section 40. The information processing unit 30 controls the operation of each component within the ultrasound diagnostic apparatus 12.

The ultrasound image formation section 38 forms a plurality of ultrasound image based on the plurality of pieces of input reception frame data. In the embodiment, a real-time tomographic image serving as a video image is composed of a plurality of ultrasound images.

In the embodiment, the reference image formation section 40 forms the reference image representing the same tissue as the real-time tomographic image. As will be described in detail below, cross-section data corresponding to the beam scanning plane is extracted from the selected specific volume data, and the reference image as a tomographic image is formed based on the extracted cross-section data. The reference image is a past image to be compared with the real-time tomographic image. The reference image formation section 40 specifies the position of the beam scanning plane within the three-dimensional space based on the position information obtained from the positioning system. That is, the reference image formation section 40 specifies the position of the cross-section data extracted from the volume data based on the position information.

The acquisition section 44 acquires the data group from the server 18 at a predetermined timing in the ultrasound examination and stores the data group in a storage unit 48. The data group is composed of a plurality of pieces of volume data obtained from a target (specific subject) of the current ultrasound examination. Specifically, the acquisition section 44 acquires the data group of the specific subject from the server by transmitting identification information of the specific subject to the server.

The ultrasound examination is usually composed of a plurality of steps arranged in chronological order. In the embodiment, the plurality of steps include a step of executing the multi-image display mode (a multi-image display step). In the multi-image display mode, a reference image formed based on volume data acquired by another modality is displayed. As the reference image, a past ultrasound image (for example, a tomographic image) may be displayed. In any case, by observing two images (the real-time tomographic image and the reference image) representing the same tissue, accurate diagnosis and evaluation of the tissue can be performed.

The deletion section 46 executes processing of automatically deleting the data group acquired from the server. The deletion section 46 has the first deletion function of deleting one or a plurality of pieces of data satisfying the deletion condition within the data group at the end of the multi-image display mode, and the second deletion function of deleting one or a plurality of pieces of data remaining within the data group at the end of the ultrasound examination. Through the data deletion by the deletion section 46, it is possible to prevent a plurality of pieces of data with low potential for use from remaining for a long period in the storage unit 48, which will be described below. Alternatively, it is possible to prevent the burden on the user in a case of individually deleting the data.

In the embodiment, in addition to the function of selectively deleting data as described above, the deletion section 46 also has a function of collectively deleting the entire data group at the end of the multi-image display mode. The data may be automatically deleted not at the end of the multi-image display mode but after the end. For example, the data may be automatically deleted at a point in time when a predetermined time has elapsed from the end of the multi-image display mode.

The storage unit 48 serving as the local storage unit is connected to the information processing unit 30. The storage unit 48 is composed of a semiconductor memory, a hard disk, or the like. The storage unit 48 stores a management table 50, a data group 52, an ultrasound image data group 54, and the like.

The data group 52 is composed of, for example, a plurality of pieces of volume data downloaded from the server. At the start of the ultrasound examination of the subject, all of the volume data with potential for reference is pre-acquired as the data group 52 for that subject, and the data group 52 is stored in the storage unit 48. The upper limit of the number of pieces of volume data to be acquired may be designated by the user. Each individual volume data is composed of, for example, 100 or more pieces of slice data, and the storage capacity thereof is very large. Therefore, each individual volume data is deleted as needed according to the potential for future use of the individual volume data.

The management table 50 is a table for managing the data group 52 acquired from the server. The management table 50 has a flag for managing the presence or absence of a predetermined user operation for each individual volume data. This will be described in detail below. The ultrasound image data group 54 is composed of a plurality of pieces of ultrasound image data acquired by the ultrasound diagnostic apparatus 12.

An operation panel 56, a display 58, a communication unit 60, and the like are connected to the information processing unit 30. The operation panel 56 is an input device that includes a plurality of switches, a trackball, a keyboard, and the like. The display 58 is composed of a liquid crystal display, an organic EL display, or the like.

For example, the real-time tomographic image, which is a real-time ultrasound image, and the reference image, such as a CT image or an MR image, corresponding to the tomographic image are juxtaposed and displayed on the display 58 during the execution of the multi-image display mode. A plurality of reference images may be displayed together with the real-time tomographic image. The information processing unit 30 is connected to the network 20 via the communication unit. The network 20 is, for example, a LAN. The network 20 may include the Internet.

Figures 2, 3, 4:
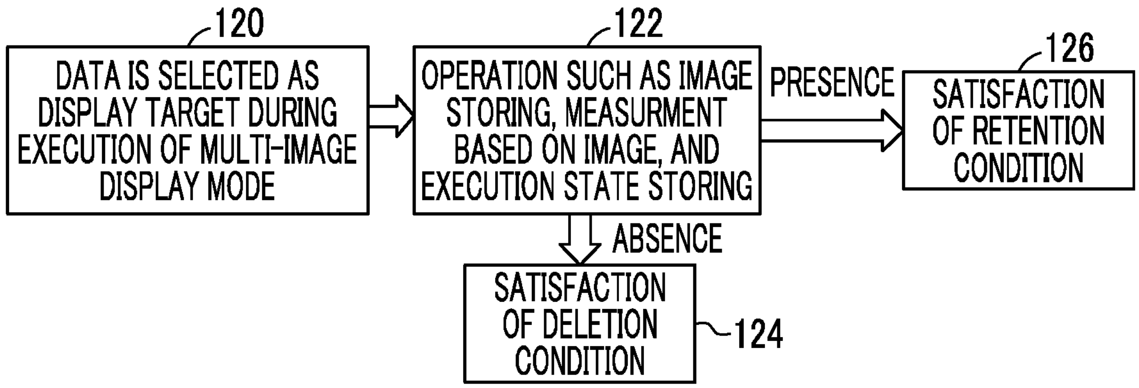
FIG. 2 is a diagram showing a database provided in a server.
FIG. 3 is a diagram showing a deletion condition and a retention condition.
FIG. 4 is a diagram showing a configuration example of a management table.

FIG. 2 shows an example of a management table 62 provided in the server 18. Each individual data uploaded to the server 18 is managed using the management table 62. The management table 62 has a plurality of records 64. Each record 64 is composed of a plurality of pieces of information. In the shown example, the plurality of pieces of information include a data ID 66, a subject ID 68, a subject name 70, an examination date 72, a modality type 74, a data type 76, and the like. The modality type 74 is information indicating the type of the medical apparatus from which the data has been acquired. Two-dimensional data, three-dimensional data, and the like are managed as the data type 76.

The server may perform filtering of the data group to be transferred to the ultrasound diagnostic apparatus, or the ultrasound diagnostic apparatus may perform filtering of the data group acquired from the server.

FIG. 3 shows an example of the deletion condition and the retention condition to be applied to the data group in the ultrasound diagnostic apparatus. For example, a reference numeral 120 indicates a precondition. In a case where a certain piece of data is selected as a display target during the execution of the multi-image display mode, the precondition is satisfied. As indicated by a reference numeral 122, it is determined whether or not the user has performed a predetermined operation on the selected data. Examples of the predetermined operation include an image storing operation, a measurement based on an image, an operation of storing an execution state of a plurality of screen displays, and the like. The predetermined operation may be defined by the user.

In a case where it is determined that a predetermined operation has been performed on the data satisfying the precondition, the satisfaction of the retention condition is determined as indicated by a reference numeral 126. On the other hand, in a case where it is determined that the predetermined operation has not been performed on the data satisfying the precondition, the satisfaction of the deletion condition is determined as indicated by a reference numeral 124. In that case, the data is automatically deleted from the storage unit at the end of the multi-image display mode. In a case where the retention condition is satisfied, the data is deleted at the end of the ultrasound examination.

However, the deletion thereof may be prohibited to maintain the remaining state of the data. In that case, for example, the data may be automatically deleted after a lapse of a certain period from the end of the examination. Since the same data still exists in the server even in a case where the data is deleted, the data can be reacquired.

FIG. 4 shows an example of the management table 50 provided in the ultrasound diagnostic apparatus. The management table 50 has a plurality of records 78 corresponding to a plurality of pieces of data constituting the data group. Each record 78 has a plurality of pieces of information. In the shown example, the plurality of pieces of information include a subject ID 80, a subject name 82, an examination date 84, a modality type 86, and a data type 88, and further includes an operation flag 90.

The "1" as the operation flag 90 indicates that the predetermined operation has been performed after the precondition has been satisfied. The "0" as the operation flag 90 indicates that the precondition is not satisfied, or the precondition has been satisfied but the predetermined operation has not been performed. At the end of the multi-image display mode, the deletion section refers to the operation flag 90 for each data acquired from the server, thereby specifying the data satisfying the deletion condition and the data satisfying the retention condition.

Figure 5:
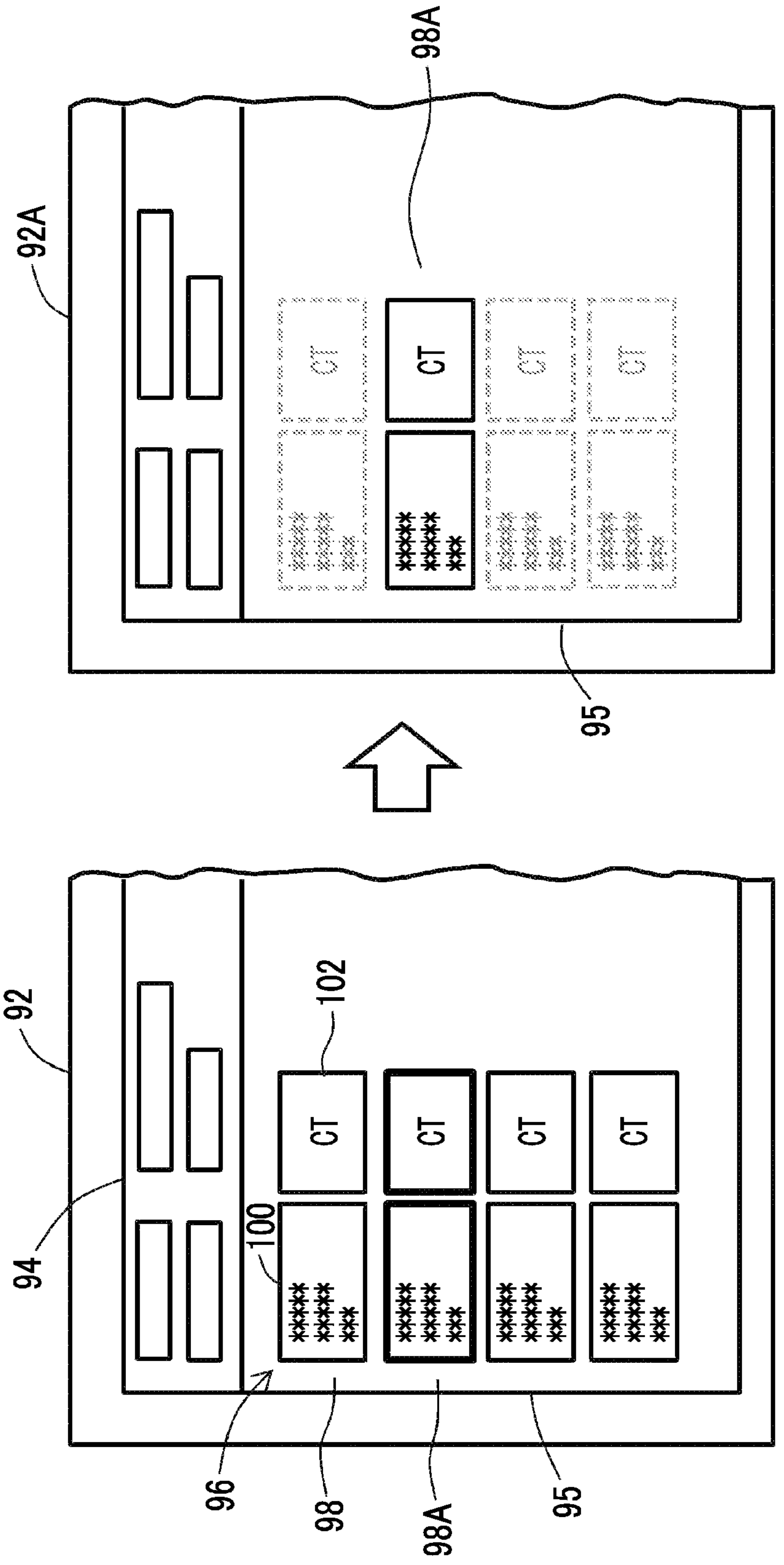
FIG. 5 is a diagram showing a storage state of a local storage unit.

An image 92 is shown in FIG. 5. The image 92 shows the storage state of the data group downloaded from the server. The image 92 includes a field 94 for inputting search conditions and a field 95 for showing search results. The field 95 includes an item column 96. The item column 96 is composed of a plurality of items 98. Each item 98 includes information 100 for specifying the downloaded data and a thumbnail image 102 that represents the downloaded data. In the shown example, four pieces of volume data are downloaded and four thumbnail images representing them are displayed. Each thumbnail image is created based on the cross-section data representing the volume data.

The deletion processing is automatically executed at the end of the multi-image display mode. An image 92A shows a state after the deletion. Only one item 98A is displayed in the field 95. The other three items are hidden. This indicates that the three pieces of downloaded volume data have already been deleted.

Figure 6:
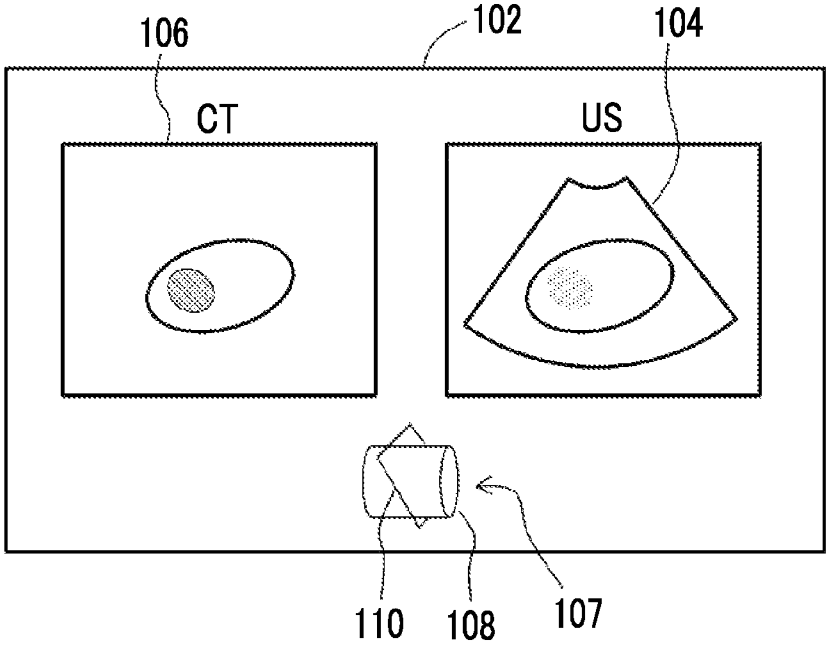
FIG. 6 is a diagram showing an example of a multi-image display.

FIG. 6 shows an example of an image displayed in the multi-image display mode. An image 102 includes a real-time tomographic image 104 and a reference image 106. The real-time tomographic image 104 is a current ultrasound image generated through transmission and reception of ultrasound waves. The reference image 106 is, for example, a tomographic image generated from the cross-section data corresponding to the beam scanning plane in CT volume data. The tomographic image represents the same tissue as the tissue appearing in the real-time tomographic image 104.

The image 102 includes a three-dimensional body mark 107. The three-dimensional body mark 107 is a guidance image and includes an image 108 that schematically represents a tissue and an image 110 that schematically represents a beam scanning plane or a cross-section including the beam scanning plane.

Figure 7:
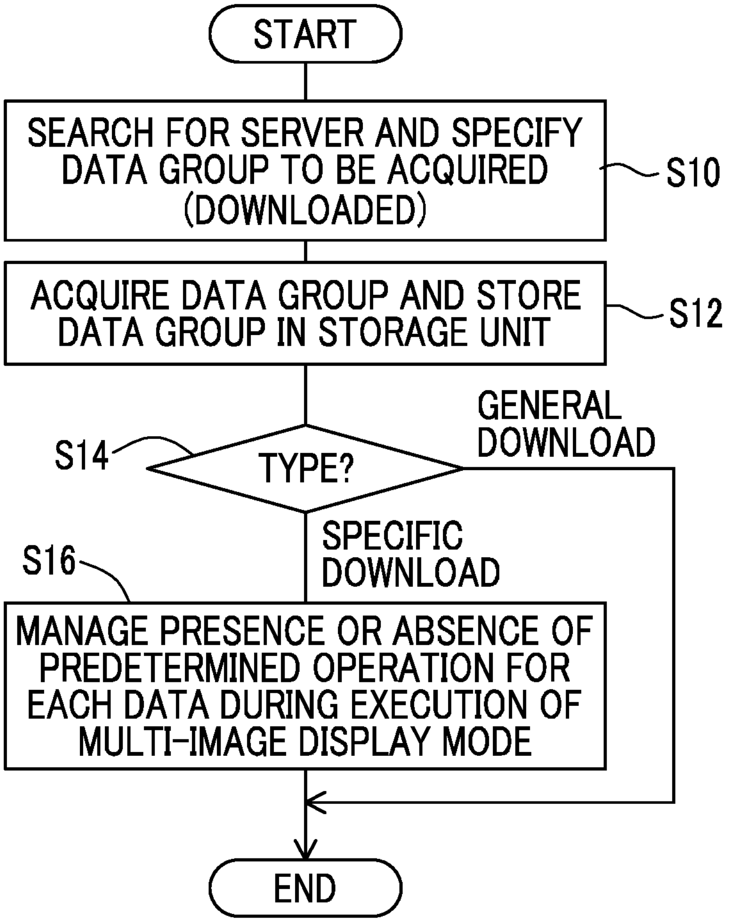
FIG. 7 is a flowchart showing an operation of an acquisition section.

FIG. 7 shows the operation of the acquisition section in the embodiment. For example, at the start of execution of the multi-image display mode, in S10, the server is searched for, whereby the data group to be acquired from the server is specified. For example, the data group is composed of a plurality of pieces of data acquired from a specific subject who is currently undergoing the ultrasound examination. In the embodiment, each data is volume data acquired by another modality. In S12, a data group is acquired (downloaded) from the server, and the data group is stored in the storage unit (local storage unit).

In S14, a download type is determined. A specific download is determined as the download type in a case where the data group is acquired during the execution process of the multi-image display mode, whereas a general download is determined in a case where the data group is acquired irrespective of the multi-image display mode. In a case where the specific download is performed, in S16, the presence or absence of the predetermined operation is managed for each of the data used during the execution of the multi-image display mode. Specifically, the contents of the flag are managed on the management table. On the other hand, in a case where the general download is performed, the management shown in S16 is not performed, and in that case, the automatic deletion is not performed. This is because there is a probability of using the data group in other applications or other modes. Of course, in such a case, the data group acquired at the end of the ultrasound examination may be deleted all at once. The user may select in advance whether or not to execute the step of S16.

Figure 8:
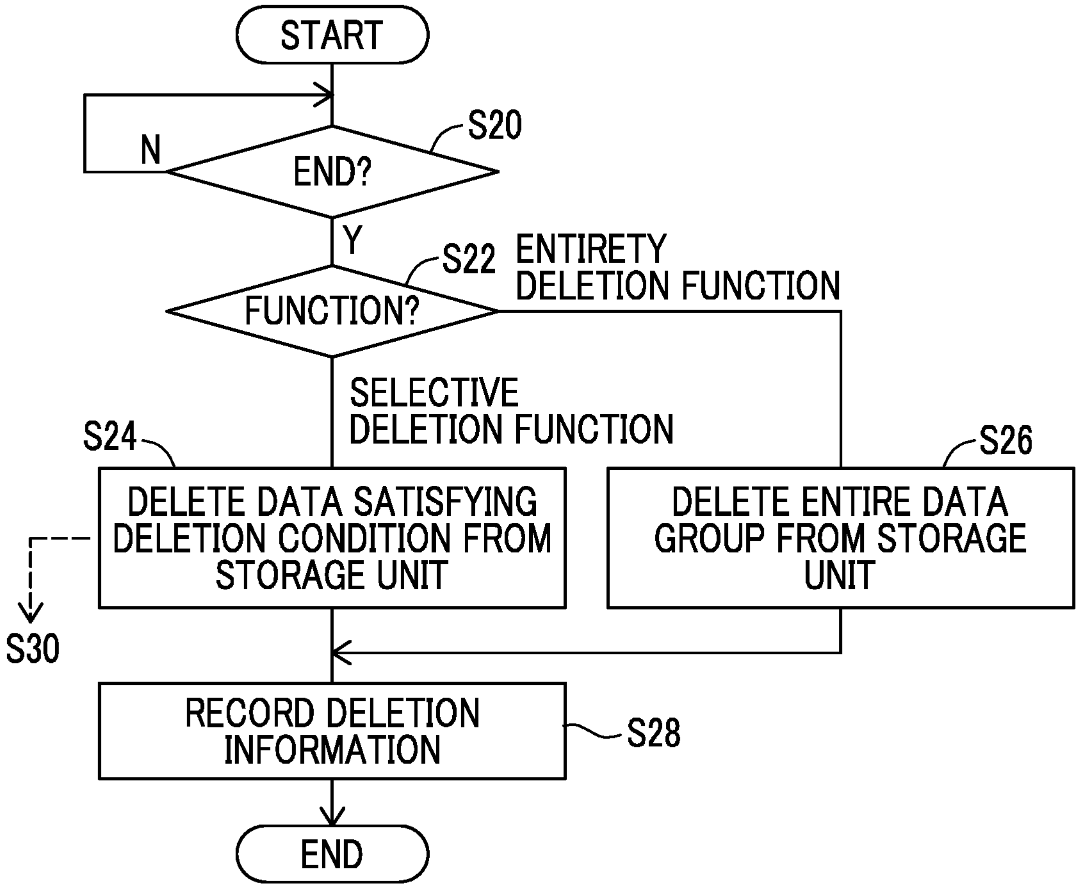
FIG. 8 is a flowchart showing a basic operation of a deletion section.

FIG. 8 shows the operation of the deletion section in the embodiment. In a case where the end of the multi-image display mode is determined in S20, a function selected in advance by the user among the selective deletion function and the entirety deletion function in S22 is identified. In a case where the selective deletion function is selected, in S24, only the data satisfying the deletion condition is deleted from the storage unit. That is, data with low potential for future use is deleted.

On the other hand, in a case where the entirety deletion function is selected, in S28, the entire data group is deleted from the storage unit. In S28, deletion information is recorded as a log.

In a case where S24 is performed, the remaining data is deleted from the storage unit at the end of the ultrasound examination (S30). However, in a case where such deletion is restricted by the user, the storage state of the remaining data is maintained.

According to the above-described embodiment, it is possible to prevent the volume data group acquired from the server from being stored in the local storage unit for a long time.

What is claimed is:

1. An ultrasound diagnostic apparatus comprising:

a local storage unit;

an acquisition section configured to download a data group from a server and store the downloaded data group in the local storage unit in a current ultrasound examination, the local storage unit storing a management table registering, for each data constituting the downloaded data group, a flag indicating presence or absence of a predetermined operation on the data;

a controller configured to display, during execution of a multi-image display mode in the current ultrasound examination, (i) a real-time ultrasound image generated through transmission and reception of an ultrasound wave and (ii) a reference image generated based on data selected from the downloaded data group stored in the local storage unit, the downloaded data group comprising a plurality of pieces of data obtained from within a body of a specific subject in past examinations, and the real-time ultrasound image being a real-time tomographic image representing a tissue on a beam scanning plane formed within the body of the same specific subject; and a deletion section configured to automatically delete, without a delete operation by a user, data satisfying a deletion condition within the downloaded data group stored in the local storage unit, from the local storage unit at or after an end of the multi-image display mode, the data satisfying the deletion condition being data (a) which has been selected as a display target during the execution of the multi-image display mode in the current ultrasound examination and (b) on which the predetermined operation has not been performed during the execution of the multi-image display mode in the current ultrasound examination.

2. The ultrasound diagnostic apparatus according to claim 1, wherein the downloaded data group includes volume data obtained from within the body of the specific subject, and cross-section data corresponding to the beam scanning plane is extracted from volume data serving as the selected data, and the reference image is generated and displayed based on the cross-section data, during the execution of the multi-image display mode.

3. The ultrasound diagnostic apparatus according to claim 1, wherein the deletion section is further configured to:

delete the data satisfying the deletion condition from the local storage unit at the end of the multi-image display mode; and delete data remaining within the downloaded data group stored in the local storage unit at an end of the current ultrasound examination including a step of executing the multi-image display mode.

4. The ultrasound diagnostic apparatus according to claim 1, wherein the deletion section is further configured to, only in a case where the downloaded data group is downloaded from the server during the execution of the multi-image display mode, delete the data satisfying the deletion condition from the local storage unit at or after the end of the multi-image display mode.

5. The ultrasound diagnostic apparatus according to claim 1, wherein the deletion section is further configured to specify the data satisfying the deletion condition by referring to the management table.

6. The ultrasound diagnostic apparatus according to claim 1, wherein the deletion section comprises:

a first deletion function of deleting the data satisfying the deletion condition from the local storage unit at the end of the multi-image display mode; and a second deletion function of deleting the entire downloaded data group from the local storage unit at the end of the multi-image display mode, and the first deletion function or the second deletion function is selected by a user.

7. A data processing method performed by an ultrasound diagnostic apparatus, the data processing method comprising:

a step of downloading a data group from a server and storing the downloaded data group in a local storage unit of the ultrasound diagnostic apparatus in a current ultrasound examination;

a step of maintaining a management table in the local storage unit and registering in the management table, for each data constituting the downloaded data group, a flag indicating presence or absence of a predetermined operation on the data;

a step of displaying, during execution of a multi-image display mode in the current ultrasound examination, (i) a real-time ultrasound image generated through transmission and reception of an ultrasound wave and (ii) a reference image generated based on data selected from the downloaded data group stored in the local storage unit, the downloaded data group comprising a plurality of pieces of data obtained from within a body of a specific subject in past examinations, and the real-time ultrasound image being a real-time tomographic image representing a tissue on a beam scanning plane formed within the body of the same specific subject; and a step of automatically deleting, without a delete operation by a user, data satisfying a deletion condition within the downloaded data group stored in the local storage unit, from the local storage unit at or after an end of the multi-image display mode, the data satisfying the deletion condition being data (a) which has been selected as a display target during the execution of the multi-image display mode in the current ultrasound examination and (b) on which the predetermined operation has not been performed during the execution of the multi-image display mode in the current ultrasound examination.

8. The data processing method according to claim 7, wherein the downloaded data group includes volume data obtained from within the body of the specific subject, and cross-section data corresponding to the beam scanning plane is extracted from volume data serving as the selected data, and the reference image is generated and displayed based on the cross-section data, during the execution of the multi-image display mode.

9. The data processing method according to claim 7, wherein the data satisfying the deletion condition from the local storage unit is deleted at the end of the multi-image display mode, and the data processing method further comprises a step of executing the multi-image display mode.

10. The data processing method according to claim 7, wherein only in a case where the downloaded data group is downloaded from the server during the execution of the multi-image display mode, the data satisfying the deletion condition is deleted from the local storage unit at or after the end of the multi-image display mode.

11. The data processing method according to claim 7, further comprising:

a step of specifying the data satisfying the deletion condition by referring to the management table.

12. The data processing method according to claim 7, further comprising:

providing a first deletion function of deleting the data satisfying the deletion condition from the local storage unit at the end of the multi-image display mode;

providing a second deletion function of deleting the entire downloaded data group from the local storage unit at the end of the multi-image display mode; and selecting by a user the first deletion function or the second deletion function.

13. An ultrasound diagnostic apparatus comprising:

an acquisition section configured to download a data group from a server;

a storage unit storing a management table registering, for each data constituting the downloaded data group, a flag indicating presence or absence of a predetermined operation on the data;

a controller configured to display, during execution of a multi-image display mode in a current ultrasound examination, (i) a real-time ultrasound image generated through transmission and reception of an ultrasound wave and (ii) a reference image generated based on data selected from the downloaded data group, the downloaded data group comprising a plurality of pieces of data obtained from within a body of a specific subject in past examinations, and the real-time ultrasound image being a real-time tomographic image representing a tissue on a beam scanning plane formed within the body of the same specific subject; and a deletion section configured to automatically delete, without a delete operation by a user, data satisfying a deletion condition within the downloaded data group, at or after an end of the multi-image display mode, the data satisfying the deletion condition being data (a) which has been selected as a display target during the execution of the multi-image display mode in the current ultrasound examination and (b) on which the predetermined operation has not been performed during the execution of the multi-image display mode in the current ultrasound examination.

* * * * *